(12) United States Patent
Long et al.

(10) Patent No.: US 9,926,263 B2
(45) Date of Patent: Mar. 27, 2018

(54) SOLVENT MEDIUM FOR DIAZOTIZATION REACTION

(71) Applicant: NANTONG TEXTILE & SILK INDUSTRIAL TECHNOLOGY RESEARCH INSTITUTE, Nantong, Jiangsu (CN)

(72) Inventors: Jiajie Long, Zhangjiagang (CN); Xiaochen Wei, Zhangjiagang (CN); Ming Shen, Zhangjiagang (CN)

(73) Assignee: NANTONG TEXTILE & SILK INDUSTRIAL TECHNOLOGY RESEARCH INSTITUTE, Nantong (CN)

( * ) Notice: Subject to any disclaimer, the term of this patent is extended or adjusted under 35 U.S.C. 154(b) by 0 days.

(21) Appl. No.: 15/119,746

(22) PCT Filed: Jun. 25, 2014

(86) PCT No.: PCT/CN2014/080730
§ 371 (c)(1),
(2) Date: Aug. 18, 2016

(87) PCT Pub. No.: WO2015/188401
PCT Pub. Date: Dec. 17, 2015

(65) Prior Publication Data
US 2017/0073303 A1 Mar. 16, 2017

(30) Foreign Application Priority Data

Jun. 10, 2014 (CN) .......................... 2014 1 0254599

(51) Int. Cl.
C07C 245/20 (2006.01)
C07B 43/00 (2006.01)
C09K 3/00 (2006.01)

(52) U.S. Cl.
CPC ............ C07C 245/20 (2013.01); C07B 43/00 (2013.01); C09K 3/00 (2013.01)

(58) Field of Classification Search
CPC ................................................. C07C 245/20
See application file for complete search history.

(56) References Cited

U.S. PATENT DOCUMENTS

2006/0178268 A1* 8/2006 Kros ...................... C05G 3/007
504/101

FOREIGN PATENT DOCUMENTS

| CN | 1099776 A | 3/1995 |
| CN | 1952015 A | 4/2007 |
| CN | 101117446 A | 2/2008 |
| CN | 101333339 A | 12/2008 |
| CN | 103265820 A | 8/2013 |

OTHER PUBLICATIONS

Wang, Jinxian et al., "Four-component One-pot Synthesis of Polyhydroquinolines in PEG-400-water System", Journal of Northwest Normal University (Natural Science), vol. 47, No. 2, Mar. 15, 2011 (Mar. 15, 2011), pp. 64-68.
Jouyban, A. et al., "Solubility of Benzodiazepines in Polyethylene Glycol 200 + Water Mixtures at 303.2 K", J. Chem. Eng. Data, vol. 55, No. 1, Jun. 15, 2009 (Jun. 15, 2009), pp. 519-522.
Azar, V.P. et al., "Thermodynamic Studies of Fluphenazine Decanoate Solubility in PEG 200 + water Mixtures", Fluid Phase Equilibria, vol. 330, Jun. 15, 2012 (Jun. 15, 2012), pp. 36-43.
Ahumada, E.A. et al., "Solution Thermodynamics of Acetaminophen in Some Peg 400 + water Mixtures", Fluid Phase Equilibria, vol. 332, Jul. 14, 2012 (Jul. 14, 2012), pp. 120-127.
Chavan, H.V. et al., "Polyethylene Glycol in Water: A Simple, Efficient and Green Protocol for the Synthesis of Quinoxalines", J. Chem. Sci., No. 4, vol. 123, Jul. 31, 2011 (Jul. 31, 2011), pp. 477-483.
Chavan, H.V. et al., "Acoustic Emission during Cooling and Heating of Aqueous Solutions of Polyethylene Glycols of Molecular Masses from 300 to 3000", Cryobiology, vol. 47, Aug. 31, 2003 (Aug. 31, 2003), pp. 40-43.

* cited by examiner

Primary Examiner — Peter F Godenschwager
(74) Attorney, Agent, or Firm — SZDC Law PC

(57) ABSTRACT

A solvent medium for diazotization reaction includes a mixed solution of polyethylene glycol and water. The molecular weight of polyethylene glycol is 200-600, and the volume ratio of polyethylene glycol and water is 1:0.4-1.5. The mixed solution also includes hydrochloric acid or sulfuric acid, and the concentration of $H^+$ in the mixed solution is 0.32-1.72 mol $L^{-1}$.

4 Claims, No Drawings

SOLVENT MEDIUM FOR DIAZOTIZATION REACTION

This application is a national phase application of PCT/CN2014/080730, filed on Jun. 25, 2014, which claims the benefit of Chinese Patent Application No. 201410254599.1, filed on Jun. 10, 2014, which is incorporated by reference for all purposes as if fully set forth herein.

FIELD OF THE INVENTION

The present invention relates to the field of dye synthesis, and more particularly to a solvent medium for diazotization reaction.

DESCRIPTION OF THE RELATED ART

Azo disperse dyes are widely used in dyeing textiles such as synthetic fibers, due to its' simple preparation method, complete chromatography and low cost. Furthermore, Azo disperse dyes have also been extensively used in pigments, paper and the like.

Diazotization and coupling reactions are two most important steps of preparation of azo disperse dyes. The principle of diazotization reaction is as following: a diazotization reagent such as sodium nitrite in-situ or on-site generates a electrophilic reagent in an acidic condition, and the electrophilic reagent attack amino groups of aromatic primary amines to generate a nitrosamine, then the nitrosamine rearranges and dehydrates in an acidic condition to finally obtain a diazonium salt.

Thus, the concentration and amount of an acid is one of the key factors of the diazotization reaction. And, in the diazotization reaction the acid has the following functions: (1) dissolving an aromatic primary amine; (2) reacting with a diazotization reagent such as sodium nitrite to generate nitrous acid, thereby resulting in an active electrophilic reagent; (3) taking part in the dehydration of the nitrosamine to obtain a diazonium salt. Although based on the diazotization reaction it is calculated that the molar ratio of amino groups of the aromatic primary amine and the required acid is 1:2, in actual applications, generally the acid is excessive to prevent the formation of a diazoamino compound and maintain the stability of the diazonium salt.

Furthermore, some diazo components such as 2-chloro-4-nitroaniline are weak alkaline and insoluble in a dilute acid solution, and only can react in the presence of a more active electrophilic reagent. Thus, a great amount and higher concentration of acid is required as a reaction medium in diazotization reaction of such kind of aromatic primary amines, even the diazotization reaction is directly carried out in a non-aqueous medium of concentrated sulfuric acid. A series of azo disperse dyes suitable for dyeing polyester textile materials and preparation method thereof are disclosed in China Patent CN 1099776A, wherein concentrated sulfuric acid is used as a solvent medium in the diazotization of the 2-chloro-4-nitroaniline monomer. A synthesis process of an azo disperse dye monomer is disclosed in Chinese Patent CN 101117446A, wherein the diazotization of the 2-chloro-4-nitroaniline monomer is also completed in 98% concentrated sulfuric acid.

However, in the diazotization reaction, the use of a great amount and high concentration of acid, especially the highly corrosive, strong oxidative concentrated sulfuric acid medium, will not only lead to a waste of resources and increased costs, but also put forward higher requirements for production equipment's, process operation and control as well as production safety. Meanwhile, the generated large amount of waste water will bring a great threat to the ecological environment. Thus, research and development of a solvent medium which can be used in a mild condition with a low concentration and a small amount of acid have a very important practical significance.

SUMMARY OF THE INVENTION

In order to solve the above technical problems, one object of the invention is to provide a solvent medium for diazotization reaction. The solvent medium has significant phase transfer catalysis, and can effectively reduce the diazotization reaction time to accelerate the process of the diazotization reaction. The solvent medium also can effectively prevent the formation of a diazoamino compound and maintain the stability of a diazonium salt, thereby improving the yield of the diazonium salt and ensure the good quality of the diazonium salt. Furthermore, by means of the solvent medium, the diazotization reaction has a simple operation process, a low-cost production device as well as high safety, and can reduce the pollution of environment, thus, the solvent medium of the invention make the production more environmentally friendly.

The solvent medium for diazotization reaction of the invention comprises a mixed solution of polyethylene glycol and water, the molecular weight of polyethylene glycol is 200-600, and the volume ratio of polyethylene glycol and water is 1:0.4-1.5.

Preferably, the molecular weight of polyethylene glycol is 200-400, and the volume ratio of polyethylene glycol and water is 1:0.4-1.25.

Preferably, the molecular weight of polyethylene glycol is 400-600, and the volume ratio of polyethylene glycol and water is 1:1.0-1.5.

Preferably, the mixed solution also includes hydrochloric acid or sulfuric acid, so that the $H^+$ concentration of the mixed solution is 0.32-1.72 mol $L^{-1}$.

More preferably, the $H^+$ concentration of the mixed solution is 0.35-1.72 mol $L^{-1}$.

More preferably, the $H^+$ concentration of the mixed solution is 0.32-0.39 mol $L^{-1}$.

The solvent medium for diazotization reaction of the present invention is a mixed solution of polyethylene glycol and water, the molecular weight of polyethylene glycol is 200-600, and the volume ratio of polyethylene glycol and water is 1:0.4-1.5. Experiments show that, polyethylene glycol with a molecular weight of 200-600 has significant phase transfer catalysis, and can effectively reduce the diazotization reaction time to accelerate the process of the diazotization reaction. The solvent medium also can effectively prevent the formation of a diazoamino compound and maintain the stability of a diazonium salt, thereby improving the yield of the diazonium salt and ensure the good quality of the diazonium salt. Furthermore, by means of the solvent medium, the diazotization reaction can utilize a simple operation process and a low-cost production device. The polyethylene glycol component in solvent medium is less volatile, non-irritant, non-toxic ecologically, has good solubility and dispersion properties, and can dissolve and disperse the weak alkaline and insoluble diazo components well and thus can effectively achieve the dissolution effects of reactants in concentrated acids such as concentrated sulfuric acid. This will avoid the addition of the high concentration and large amount of acid in diazotization reaction of prior art, especially the highly corrosive, strong oxidative concentrated sulfuric acid medium. Thus, the solvent medium of the invention will not only reduce the waste of resources and production costs, but also simplify the requirements on production equipment's, process operation and control and production safety. Meanwhile, the production process will not produce a lot of acid-containing wastewater and reduce the pollution of the environment, this is more environmentally friendly.

DESCRIPTION OF THE PREFERRED EMBODIMENTS

The invention will be further illustrated in more detail with reference to embodiments. It is noted that, the following embodiments only are intended for the purpose of illustration and are not intended to limit the scope of the invention.

The solvent medium for diazotization reaction of the invention comprises a mixed solution of polyethylene glycol and water, the molecular weight of polyethylene glycol is 200-600, and the volume ratio of polyethylene glycol and water is 1:0.4-1.5.

Preferably, the molecular weight of polyethylene glycol is 200-400, and the volume ratio of polyethylene glycol and water is 1:0.4-1.25.

Preferably, the molecular weight of polyethylene glycol is 400-600, and the volume ratio of polyethylene glycol and water is 1:1.0-1.5.

Preferably, the mixed solution also includes hydrochloric acid or sulfuric acid, so that the $H^+$ concentration of the mixed solution is 0.32-1.72 mol $L^{-1}$.

More preferably, the $H^+$ concentration of the mixed solution is 0.35-1.72 mol $L^{-1}$.

More preferably, the $H^+$ concentration of the mixed solution is 0.32-0.39 mol $L^{-1}$.

The solvent medium for diazotization reaction of the present invention utilizes a mixed solution of polyethylene glycol and water, the molecular weight of polyethylene glycol is 200-600, and the volume ratio of polyethylene glycol and water is 1:0.4-1.5. Experiments show that, polyethylene glycol with a molecular weight of 200-600 has significant phase transfer catalysis, and can effectively reduce the diazotization reaction time to accelerate the process of the diazotization reaction. The solvent medium also can effectively prevent the formation of a diazoamino compound and maintain the stability of a diazonium salt, thereby improving the yield of the diazonium salt and ensure the good quality of the diazonium salt. Furthermore, by means of the solvent medium, the diazotization reaction can utilize a simple operation process and a low-cost production device. The polyethylene glycol component in solvent medium is less volatile, non-irritant, non-toxic ecologically, has good solubility and dispersion properties, and can dissolve and disperse the weak alkaline and insoluble diazo components well, and thus can effectively achieve the dissolution effects of reactants in concentrated acids such as concentrated sulfuric acid. This will avoid the addition of large amount of the high concentration and large amount of acid in diazotization reaction of prior art. Thus, the solvent medium is an environmentally friendly and safe reaction medium, and can reduce the pollution of environment.

Embodiment 1

70 ml of polyethylene glycol 200 (200 represents the molecular weight of polyethylene glycol) was added to 28 ml of deionized water, after mixing uniformly under stirring a solvent medium is obtained. Then 0.345 g (0.002 mol) 2-chloro-4-nitroaniline was dissolved in the solvent medium and 1.6 ml (0.02 mol) of concentrated hydrochloric acid was added, the resulting solution was transferred to a three-necked flask equipped with a magnetic stirrer and a thermometer, and then was cooled to 0-5° C. The $H^+$ concentration of the solvent medium was 0.68 mol $L^{-1}$. After stirring evenly, 5 ml 3.04% (0.0022 mol) of sodium nitrite aqueous solution was slowly added to the reaction solution. 2.5 h later, 5 ml 0.24% (0.0002 mol) of urea aqueous solution was added to decompose the excessive nitrous acid, stirring was continued for 15 mins to prepare a diazonium salt solution.

0.205 g (0.0022 mol) aniline dissolved in 5 ml of polyethylene glycol 200 was slowly and dropwise added to the above diazonium salt solution, and 30% NaOH aqueous solution was used to adjust the reaction solution so that the pH is equal to 6, and the reaction is performed at 0-5° C. for 3 h. Subsequently, the reaction solution was diluted with deionized water, filtered by suction and washed until neutral, then the collected product was dried under vacuum at 50° C. to get a crude product of a specialized dye precursor, and the yield is 82.2%.

Embodiment 2

63 ml of polyethylene glycol 200 (200 represents the molecular weight of polyethylene glycol) was added to 38 ml of deionized water, after mixing uniformly under stirring a solvent medium is obtained. Then 0.345 g (0.002 mol) 2-chloro-4-nitroaniline was dissolved in the solvent medium and 1.6 ml (0.02 mol) of concentrated hydrochloric acid was added, the resulting solution was transferred to a three-necked flask equipped with a magnetic stirrer and a thermometer, and then was cooled to 0-5° C. The $H^+$ concentration of the solvent medium was 0.51 mol $L^{-1}$. After stirring evenly, 5 ml 3.04% (0.0022 mol) of sodium nitrite aqueous solution was slowly added to the reaction solution. 2.5 h later, 5 ml 0.24% (0.0002 mol) of urea aqueous solution was added to decompose the excessive nitrous acid, stirring was continued for 15 mins to prepare a diazonium salt solution.

0.205 g (0.0022 mol) aniline dissolved in 5 ml of polyethylene glycol 200 was slowly and dropwise added to the above diazonium salt solution, and 30% NaOH aqueous solution was used to adjust the reaction solution so that the pH is equal to 6, and the reaction is performed at 0-5° C. for 3 h. Subsequently, the reaction solution was diluted with deionized water, filtered by suction and washed until neutral, then the collected product was dried under vacuum at 50° C. to get a crude product of a specialized dye precursor, and the yield is 92.3%.

Embodiment 3

55 ml of polyethylene glycol 300 (300 represents the molecular weight of polyethylene glycol) was added to 44 ml of deionized water, after mixing uniformly under stirring a solvent medium is obtained. Then 0.345 g (0.002 mol) 2-chloro-4-nitroaniline was dissolved in the solvent medium and 1.6 ml (0.02 mol) of concentrated hydrochloric acid was added, the resulting solution was transferred to a three-necked flask equipped with a magnetic stirrer and a thermometer, and then was cooled to 0-5° C. The $H^+$ concentration of the solvent medium was 0.44 mol $L^{-1}$. After stirring evenly, 5 ml 3.04% (0.0022 mol) of sodium nitrite aqueous solution was slowly added to the reaction solution. 2.5 h later, 5 ml 0.24% (0.0002 mol) of urea aqueous solution was added to decompose the excessive nitrous acid, stirring was continued for 15 mins to prepare a diazonium salt solution.

0.205 g (0.0022 mol) aniline dissolved in 5 ml of polyethylene glycol 300 was slowly and dropwise added to the above diazonium salt solution, and 30% NaOH aqueous solution was used to adjust the reaction solution so that the pH is equal to 6, and the reaction is performed at 0-5° C. for 3 h. Subsequently the reaction solution was diluted with deionized water, filtered by suction and washed until neutral, then the collected product was dried under vacuum at 50° C. to get a crude product of a specialized dye precursor, and the yield is 94.2%.

Embodiment 4

50 ml of polyethylene glycol 200 (200 represents the molecular weight of polyethylene glycol) was added to 50 ml of deionized water, after mixing uniformly under stirring a solvent medium is obtained. Then 0.345 g (0.002 mol) 2-chloro-4-nitroaniline was dissolved in the solvent medium and 1.6 ml (0.02 mol) of concentrated hydrochloric acid was added, the resulting solution was transferred to a three-necked flask equipped with a magnetic stirrer and a thermometer, and then was cooled to 0-5° C. The $H^+$ concentration of the solvent medium was 0.39 mol $L^{-1}$. After stirring evenly, 5 ml 3.04% (0.0022 mol) of sodium nitrite aqueous solution was slowly added to the reaction solution. 2.5 h later, 5 ml 0.24% (0.0002 mol) of urea aqueous solution was added to decompose the excessive nitrous acid, stirring was continued for 15 mins to prepare a diazonium salt solution.

0.205 g (0.0022 mol) aniline dissolved in 5 ml of polyethylene glycol 200 was slowly and dropwise added to the above diazonium salt solution, and 30% NaOH aqueous solution was used to adjust the reaction solution so that the pH is equal to 6, and the reaction is performed at 0-5° C. for 3 h. Subsequently, the reaction solution was diluted with deionized water, filtered by suction and washed until neutral, then the collected product was dried under vacuum at 50° C. to get a crude product of a specialized dye precursor, and the yield is 94.8%.

Embodiment 5

44 ml of polyethylene glycol 200 (200 represents the molecular weight of polyethylene glycol, the same below) was added to 55 ml of deionized water, after mixing uniformly under stirring a solvent medium is obtained. Then 0.345 g (0.002 mol) 2-chloro-4-nitroaniline was dissolved in the solvent medium and 1.6 ml (0.02 mol) of concentrated hydrochloric acid was added, the resulting solution was transferred to a three-necked flask equipped with a magnetic stirrer and a thermometer, and then was cooled to 0-5° C. The $H^+$ concentration of the solvent medium was 0.35 mol $L^{-1}$. After stirring evenly, 5 ml 3.04% (0.0022 mol) of sodium nitrite aqueous solution was slowly added to the reaction solution. 2.5 h later, 5 ml 0.24% (0.0002 mol) of urea aqueous solution was added to decompose the excessive nitrous acid, stirring was continued for 15 mins to prepare a diazonium salt solution.

0.205 g (0.0022 mol) aniline dissolved in 5 ml of polyethylene glycol 200 was slowly and dropwise added to the above diazonium salt solution, and 30% NaOH aqueous solution was used to adjust the reaction solution so that the pH is equal to 6, and the reaction is performed at 0-5° C. for 3 h. Subsequently, the reaction solution was diluted with deionized water, filtered by suction and washed until neutral, then the collected product was dried under vacuum at 50° C. to get a crude product of a specialized dye precursor, and the yield is 91.9%.

Embodiment 6

50 ml of polyethylene glycol 400 (400 represents the molecular weight of polyethylene glycol, the same below) was added to 50 ml of deionized water, after mixing uniformly under stirring a solvent medium is obtained. Then 0.345 g (0.002 mol) 2-chloro-4-nitroaniline was dissolved in the solvent medium and 1.6 ml (0.02 mol) of concentrated hydrochloric acid was added, the resulting solution was transferred to a three-necked flask equipped with a magnetic stirrer and a thermometer, and then was cooled to 0-5° C. The $H^+$ concentration of the solvent medium was 0.39 mol $L^{-1}$. After stirring evenly, 5 ml 3.04% (0.0022 mol) of sodium nitrite aqueous solution was slowly added to the reaction solution. 2.5 h later, 5 ml 0.24% (0.0002 mol) of urea aqueous solution was added to decompose the excessive nitrous acid, stirring was continued for 15 mins to prepare a diazonium salt solution.

0.205 g (0.0022 mol) aniline dissolved in 5 ml of polyethylene glycol 400 was slowly and dropwise added to the above diazonium salt solution, and 30% NaOH aqueous solution was used to adjust the reaction solution so that the pH is equal to 6, and the reaction is performed at 0-5° C. for 3 h. Subsequently the reaction solution was diluted with deionized water, filtered by suction and washed until neutral, then the collected product was dried under vacuum at 50° C. to get a crude product of a specialized dye precursor, and the yield is 93.7%.

Embodiment 7

40 ml of polyethylene glycol 600 was added to 60 ml of deionized water, after mixing uniformly under stirring a solvent medium is obtained. Then 0.345 g (0.002 mol) 2-chloro-4-nitroaniline was dissolved in the solvent medium and 1.6 ml (0.02 mol) of concentrated hydrochloric acid was added, the resulting solution was transferred to a three-necked flask equipped with a magnetic stirrer and a thermometer, and then was cooled to 0-5° C. The $H^+$ concentration of the solvent medium was 0.32 mol $L^{-1}$. After stirring evenly, 5 ml 3.04% (0.0022 mol) of sodium nitrite aqueous solution was slowly added to the reaction solution. 2.5 h later, 5 ml 0.24% (0.0002 mol) of urea aqueous solution was added to decompose the excessive nitrous acid, stirring was continued for 15 mins to prepare a diazonium salt solution.

0.205 g (0.0022 mol) aniline dissolved in 5 ml of polyethylene glycol 600 was slowly and dropwise added to the above diazonium salt solution, and 30% NaOH aqueous solution was used to adjust the reaction solution so that the pH is equal to 6, and the reaction is performed at 0-5° C. for 3 h. Subsequently, the reaction solution was diluted with deionized water, filtered by suction and washed until neutral, then the collected product was dried under vacuum at 50° C. to get a crude product of a specialized dye precursor, and the yield is 95.0%.

Embodiment 8

50 ml of polyethylene glycol 300 (300 represents the molecular weight of polyethylene glycol) was added to 20 ml of deionized water, after mixing uniformly under stirring a solvent medium is obtained. Then 0.345 g (0.002 mol) 2-chloro-4-nitroaniline was dissolved in the solvent medium and 1.6 ml (0.02 mol) of concentrated hydrochloric acid was added, the resulting solution was transferred to a three-necked flask equipped with a magnetic stirrer and a thermometer, and then was cooled to 0-5° C. The $H^+$ concentration of the solvent medium was 0.93 mol $L^{-1}$. After stirring evenly, 5 ml 3.18% (0.0023 mol) of sodium nitrite aqueous solution was slowly added to the reaction solution. 2 h later, 5 ml 0.36% (0.0003 mol) of urea aqueous solution was added to decompose the excessive nitrous acid, stirring was continued for 15 mins to prepare a diazonium salt solution.

0.205 g (0.0022 mol) aniline dissolved in 5 ml of polyethylene glycol 300 was slowly and dropwise added to the above diazonium salt solution, and 30% NaOH aqueous solution was used to adjust the reaction solution so that the pH is equal to 6, and the reaction is performed at 0-5° C. for 3 h. Subsequently, the reaction solution was diluted with deionized water, filtered by suction and washed until neutral, then the collected product was dried under vacuum at 50° C. to get a crude product of a specialized dye precursor, and the yield is 90.6%.

Embodiment 9

50 ml of polyethylene glycol 500 (500 represents the molecular weight of polyethylene glycol) was added to 20 ml of deionized water, after mixing uniformly under stirring a solvent medium is obtained. Then 0.345 g (0.002 mol) 2-chloro-4-nitroaniline was dissolved in the solvent medium and 2.4 ml (0.03 mol) of concentrated hydrochloric acid was added, the resulting solution was transferred to a three-necked flask equipped with a magnetic stirrer and a thermometer, and then was cooled to 0-5° C. The $H^+$ concentration of the solvent medium was 1.34 mol $L^{-1}$. After stirring evenly, 5 ml 3.18% (0.0023 mol) of sodium nitrite aqueous solution was slowly added to the reaction solution. 2 h later, 5 ml 0.36% (0.0003 mol) of urea aqueous solution was added to decompose the excessive nitrous acid, stirring was continued for 15 mins to prepare a diazonium salt solution.

0.205 g (0.0022 mol) aniline dissolved in 5 ml of polyethylene glycol 500 was slowly and dropwise added to the above diazonium salt solution, and 30% NaOH aqueous solution was used to adjust the reaction solution so that the pH is equal to 6, and the reaction is performed at 0-5 for 3 h. Subsequently, the reaction solution was diluted with deionized water, filtered by suction and washed until neutral, then the collected product was dried under vacuum at 50° C. to get a crude product of a specialized dye precursor, and the yield is 88.7%.

Embodiment 10

50 ml of polyethylene glycol 200 (200 represents the molecular weight of polyethylene glycol) was added to 20 ml of deionized water, after mixing uniformly under stirring a solvent medium is obtained. Then 0.345 g (0.002 mol) 2-chloro-4-nitroaniline was dissolved in the solvent medium and 3.2 ml (0.04 mol) of concentrated hydrochloric acid was added, the resulting solution was transferred to a three-necked flask equipped with a magnetic stirrer and a thermometer, and then was cooled to 0-5° C. The $H^+$ concentration of the solvent medium was 1.72 mol $L^{-1}$. After stirring evenly, 5 ml 3.18% (0.0023 mol) of sodium nitrite aqueous solution was slowly added to the reaction solution. 2 h later, 5 ml 0.36% (0.0003 mol) of urea aqueous solution was added to decompose the excessive nitrous acid, stirring was continued for 15 mins to prepare a diazonium salt solution.

0.205 g (0.0022 mol) aniline dissolved in 5 ml of polyethylene glycol 200 was slowly and dropwise added to the above diazonium salt solution, and 30% NaOH aqueous solution was used to adjust the reaction solution so that the pH is equal to 6, and the reaction is performed at 0-5° C. for 3 h. Subsequently, the reaction solution was diluted with deionized water, filtered by suction and washed until neutral, then the collected product was dried under vacuum at 50° C. to get a crude product of a specialized dye precursor, and the yield is 85.8%.

The above preferred embodiments are described for illustration only, and are not intended to limit the scope of the invention. It should be understood, for a person skilled in the art, that various improvements or variations can be made herein without departing from the spirit and scope of the invention, and these improvements or variations should be covered within the protecting scope of the invention.

What is claimed is:

1. A solvent medium for diazotization reaction, consisting of a mixed solution of polyethylene glycol, water, and hydrochloric acid or sulfuric acid, wherein the molecular weight of polyethylene glycol is 400-600, and the volume ratio of polyethylene glycol and water is 1:1.0-1.5.

2. The solvent medium for diazotization reaction as claimed in claim 1, wherein the concentration of $H^+$ in the mixed solution is 0.32-1.72 mol $L^{-1}$.

3. The solvent medium for diazotization reaction as claimed in claim 2, wherein the concentration of $H^+$ in the mixed solution is 0.35-1.72 mol $L^{-1}$.

4. The solvent medium for diazotization reaction as claimed in claim 2, wherein the concentration of $H^+$ in the mixed solution is 0.32-0.39 mol $L^{-1}$.

* * * * *